United States Patent
Mertens et al.

(10) Patent No.: US 7,090,814 B2
(45) Date of Patent: Aug. 15, 2006

(54) METHOD OF SYNTHESIZING SILICOALUMINOPHOSPHATE MOLECULAR SIEVES

(75) Inventors: Machteld M. Mertens, Boortmeerbeek (BE); Brita Engels, Begijnendijk (BE); Els Cecilia De Clerck, Aarschot (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/985,496

(22) Filed: Nov. 10, 2004

(65) Prior Publication Data

US 2006/0100095 A1  May 11, 2006

(51) Int. Cl.
*C01B 37/08* (2006.01)

(52) U.S. Cl. .............................. 423/306; 423/DIG. 30; 502/214

(58) Field of Classification Search ................ 423/306, 423/DIG. 30; 502/214
See application file for complete search history.

(56) References Cited

U.S. PATENT DOCUMENTS

| | | | | |
|---|---|---|---|---|
| 4,786,487 A | * | 11/1988 | Kuehl | 423/306 |
| 5,370,851 A | * | 12/1994 | Wilson | 423/305 |
| 5,609,843 A | | 3/1997 | Wendelbo | 423/306 |
| 5,663,480 A | | 9/1997 | Tsuneki et al. | 558/270 |
| 5,879,655 A | | 3/1999 | Miller et al. | 423/702 |
| 6,334,994 B1 | | 1/2002 | Wendelbo et al. | 423/718 |

FOREIGN PATENT DOCUMENTS

| | | |
|---|---|---|
| WO | 02/70407 | 9/2002 |
| WO | WO 03/057627 | 7/2003 |
| WO | WO 2005/016520 | 2/2005 |

* cited by examiner

*Primary Examiner*—David Sample

(57) ABSTRACT

In a method of synthesizing a silicoaluminophosphate molecular sieve, a synthesis mixture is prepared by combining a source of phosphorus and at least one organic directing agent; and then cooling the combination of the phosphorus source and organic directing agent to a temperature of less than or equal to 50° C., prior to introducing a source of aluminum into the combination. After addition of a source of silicon, the synthesis mixture is heated to a crystallization temperature of between about 100° C. and about 300° C. and the molecular sieve is recovered.

26 Claims, 2 Drawing Sheets

METHOD OF SYNTHESIZING SILICOALUMINOPHOSPHATE MOLECULAR SIEVES

FIELD OF INVENTION

This invention relates to a method of synthesizing silicoaluminophosphate molecular sieves and to the use of the resultant molecular sieves as catalysts for the conversion of oxygenates, particularly methanol, to olefins, particularly ethylene and propylene.

BACKGROUND OF INVENTION

Light olefins, such as ethylene, propylene, butylenes and mixtures thereof, serve as feeds for the production of numerous important chemicals and polymers. Typically, $C_2$–$C_4$ light olefins are produced by cracking petroleum refinery streams, such as $C_3$+ paraffinic feeds. In view of limited supply of competitive petroleum feeds, production of low cost light olefins from petroleum feeds is subject to waning supplies. Efforts to develop light olefin production technologies based on alternative feeds have therefore increased.

An important type of alternative feed for the production of light olefins is oxygenates, such as $C_1$–$C_4$ alkanols, especially methanol and ethanol; $C_2$–$C_4$ dialkyl ethers, especially dimethyl ether (DME), methyl ethyl ether and diethyl ether; dimethyl carbonate and methyl formate, and mixtures thereof. Many of these oxygenates may be produced from alternative sources by fermentation, or from synthesis gas derived from natural gas, petroleum liquids, carbonaceous materials, including coal, recycled plastic, municipal waste, or any organic material. Because of the wide variety of sources, alcohol, alcohol derivatives, and other oxygenates have promise as an economical, non-petroleum sources for light olefin production.

The preferred process for converting an oxygenate feedstock, such as methanol, into one or more olefin(s), primarily ethylene and/or propylene, involves contacting the feedstock with a crystalline molecular sieve catalyst composition. Among the molecular sieves that have been investigated for use as oxygenate conversion catalysts, small pore silicoaluminophosphates (SAPOs), such as SAPO-34 and SAPO-18, have shown particular promise. SAPO-34 belongs to the family of molecular sieves having the framework type of the zeolitic mineral chabazite (CHA), whereas SAPO-18 belongs to the family of molecular sieves having the AEI framework type. In addition to regular ordered silicoaluminophosphate molecular sieves, such as the AEI and CHA framework types, disordered structures, such as planar intergrowths containing both AEI and CHA framework type materials, are known and have shown activity as oxygenate conversion catalysts.

The synthesis of silicoaluminophosphate molecular sieves involves preparing a mixture comprising a source of water, a source of silicon, a source of aluminum, a source of phosphorus and at least one organic directing agent for directing the formation of said molecular sieve. The resultant mixture is then heated, normally with agitation, to a suitable crystallization temperature, typically between about 100° C. and about 300° C., and then held at this temperature for a sufficient time, typically between about 1 hour and 20 days, for crystallization of the desired molecular sieve to occur.

As is the case with the production of most synthetic molecular sieves, the synthesis of silicoaluminophosphates, and in particular intergrown forms thereof, must be closely controlled in order to avoid or minimize the production of impurity phases that can adversely affect the catalytic properties of the desired product.

According to the present invention, it has now been found that the order of addition of the starting materials, particularly of the aluminum source, and more particularly of both the aluminum source and the silicon source, and the temperature of the synthesis mixture during the addition of the starting materials can significantly impact the success of SAPO synthesis processes, particularly when conducted on a large, commercial scale. Thus, the organic directing agent used in the synthesis of silicoaluminophosphates is often a basic compound, such as a basic nitrogen compound, whereas an attractive phosphorus source is phosphoric acid or a similar phosphorus acid. The mixing of these materials can therefore generate heat and hence raise the temperature of the synthesis mixture. It has now been found that such a rise in temperature can lead to undesirable side reactions and possible production of impurity phases if the aluminum source is present in the mixture or is added thereto before the mixture has been allowed to cool.

U.S. Pat. No. 5,879,655 discloses a method for preparing a crystalline aluminophosphate or silicoaluminophosphate molecular sieve and teaches that it is critical, especially in large scale preparations, that at least some of the organic directing agent be added to the aqueous reaction mixture before a significant amount of the aluminum source is added, since otherwise the aluminum can precipitate to produce a viscous gel. In particular, the addition of the phosphorus source, aluminum source, and the organic directing agent to the aqueous reaction mixture is controlled so that the directing agent to the phosphorus molar ratio is greater than about 0.05 before the aluminum to phosphorus molar ratio reaches about 0.5.

According to Example 1 of U.S. Pat. No. 5,879,655, SAPO-11 can be produced from a synthesis mixture obtained by initially adding 17.82 kg of 86% $H_3PO_4$ to 8.59 kg of deionized ice in a stainless steel drum with external cold water cooling. 9.70 kg of aluminum isopropoxide and 21.0 kg of deionized ice are then added simultaneously in small increments over a time period of 1.5 hours with mixing using a standard mixing impeller and homogenization using a Polytron. 3.49 kg of di-n-propylamine are then added slowly with mixing. An additional 21.59 kg of aluminum isopropoxide and 18.0 kg ice are added in small increments over a time period of four hours with mixing/ homogenization, followed by an additional 3.49 kg of di-n-propylamine. 2.30 kg of fumed silica (Cabosil M-5) are then added with mixing/homogenization until >95 weight percent of the particles in the mix are smaller than 64 microns. It is reported that, during the entire procedure, the temperature of the mixture never exceeds 30° C.

Example 2 of U.S. Pat. No. 5,663,480 discloses the synthesis of a crystalline titanoaluminophosphate from a mixture obtained by placing 34.6 g of phosphoric acid (85% by weight aqueous solution) into a beaker having a capacity of 500 ml and then adding 73.6 g of tetraethylammonium hydroxide (20% by weight aqueous solution). After stirring, the resulting mixture is cooled to room temperature, and to this mixture, 18.0 g of ion-exchanged water and 21.9 g of pseudo-boehmite are added, and then 15.8 g of titanium tetraisopropoxide is also added. After the contents of the beaker are stirred for 2 hours, the resulting mixed solution is poured into an autoclave to carry out hydrothermal synthesis.

International Patent Publication No. WO 02/70407, published Sep. 12, 2002 and incorporated herein by reference, discloses a silicoaluminophosphate molecular sieve, now designated EMM-2, comprising at least one intergrown form of molecular sieves having AEI and CHA framework types, wherein said intergrown form has an AEI/CHA ratio of from about 5/95 to 40/60 as determined by DIFFaX analysis, using the powder X-ray diffraction pattern of a calcined sample of the molecular sieve. Synthesis of the intergrown material is achieved by mixing reactive sources of silicon, phosphorus and a hydrated aluminum oxide in the presence of an organic directing agent, particularly a tetraethylammonium compound. The resultant mixture is stirred and heated to a crystallization temperature, preferably from 150° C. to 185° C., and then maintained at this temperature under stirring for between 2 and 150 hours. In the Examples, various sequences are disclosed for producing the EMM-2 synthesis mixture, in which the phosphorus source is initially combined with either the directing agent or the silicon source and then the remaining components, including the aluminum component, are added without prior cooling.

U.S. Pat. No. 6,334,994, incorporated herein by reference, discloses a silicoaluminophosphate molecular sieve, referred to as RUW-19, which is also said to be an AEI/CHA mixed phase composition. DIFFaX analysis of the X-ray diffraction pattern of RUW-19 as produced in Examples 1, 2 and 3 of U.S. Pat. No. 6,334,994 indicates that these materials are characterized by single intergrown forms of AEI and CHA structure type molecular sieves with AEI/CHA ratios of about 60/40, 65/35 and 70/30. RUW-19 is synthesized by initially mixing an Al-source, particularly Al-isopropoxide, with water and a P-source, particularly phosphoric acid, and thereafter adding a Si-source, particularly colloidal silica and an organic template material, particularly tetraethylammonium hydroxide, to produce a precursor gel. The gel is then put into a steel autoclave and, after an aging period at room temperature, the autoclave is heated to a maximum temperature between 180° C. and 260° C., preferably at least 200° C., for at least 1 hour, with the autoclave being shaken, stirred or rotated during the entire process of aging and crystallization. Factors which are said to enhance the production of the mixed phase RUW-19 material include maintaining the $SiO_2$ content of the gel below 5%, reducing the liquid content of the gel after addition of the $SiO_2$ source and crystallization at temperatures of 250° C. to 260° C. Pure AEI and CHA phases are said to be favored at temperatures of 200° C. to 230° C.

SUMMARY OF INVENTION

In one aspect, the invention resides in a method of synthesizing a silicoaluminophosphate molecular sieve, the method comprising:
  (a) preparing a synthesis mixture comprising the steps of:
    (i) combining a source of phosphorus and at least one organic directing agent; and
    (ii) cooling the combination of the phosphorus source and organic directing agent to a temperature of less than or equal to 50° C., prior to introducing a source of aluminum into the combination;
  (b) heating said synthesis mixture to a crystallization temperature of between about 100° C. and about 300° C.; and
  (c) recovering said molecular sieve.

Conveniently, the combination of the phosphorus source and organic directing agent are cooled to a temperature of less than or equal to 40° C., for example less than or equal to 30° C., such as to a temperature of about 10° C. to about 30° C., prior to introducing a source of aluminum into the combination.

As used herein, the term "cooling" is intended to include not only a process in which concrete steps are taken to reduce the temperature of the combination of the phosphorus source and organic directing agent, for example by use of a heat exchanger, but also a process in which the combination is allowed to cool to ambient conditions.

Conveniently, the source of aluminum is an inorganic aluminum compound, such as a hydrated aluminum oxide and particularly boehmite or pseudoboehmite.

Conveniently, preparing said synthesis mixture further comprises introducing a source of silicon into said combination after said cooling. The silicon source can be introduced into said combination before, after or simultaneously with the introduction of said source of aluminum.

Conveniently, the method further comprises allowing the synthesis mixture to age at a temperature of between about 10° C. and about 30° C. for a time up to about 12 hours. In one embodiment, the synthesis mixture is agitated during aging.

Conveniently, the synthesis mixture is agitated during (a) and/or (b).

Conveniently, said silicoaluminophosphate molecular sieve comprises at least one of an AEI framework type molecular sieve and a CHA framework type molecular sieve.

In one embodiment, said silicoaluminophosphate molecular sieve comprises at least one intergrown phase of an AEI framework type molecular sieve and a CHA framework type molecular sieve. Conveniently, said at least one intergrown form has an AEI/CHA ratio of from about 5/95 to about 40/60, for example from about 10/90 to about 30/70, such as from about 15/85 to about 20/80, as determined by DIFFaX analysis.

In a further embodiment, the first silicoaluminophosphate molecular sieve comprises first and second intergrown forms each of an AEI framework type material and a CHA framework type material, the first intergrown form having an AEI/CHA ratio of from about 5/95 to about 40/60 as determined by DIFFaX analysis, and the second intergrown form having a different AEI/CHA ratio from said first intergrown form, such as an AEI/CHA ratio of about 50/50 as determined by DIFFaX analysis.

In a further aspect, the invention resides in a silicoaluminophosphate molecular sieve synthesized by a method described herein and its use in the conversion of an oxygenate-containing feedstock to a product comprising olefins.

DETAILED DESCRIPTION OF THE EMBODIMENTS

Figure 1A:
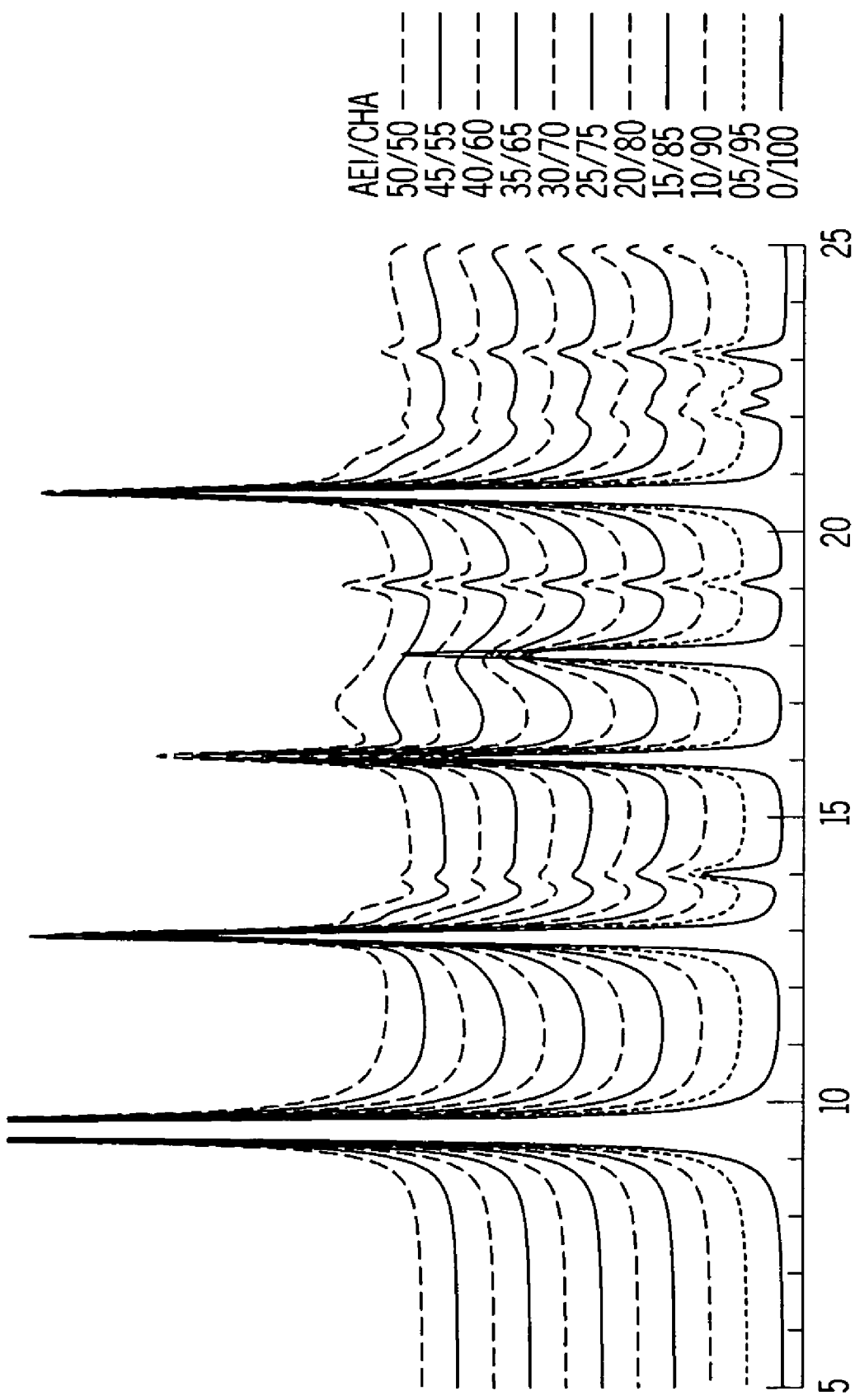
FIGS. 1a and 1b are DIFFaX simulated diffraction patterns for intergrown AEI/CHA phases having varying AEI/CHA ratios.

The present invention is directed to a method of synthesizing silicoaluminophosphate molecular sieves and, in particular, silicoaluminophosphate molecular sieves useful in the conversion of an oxygenate-containing feedstock, such as methanol, to a product comprising olefins, such as ethylene and propylene.

Molecular Sieves

Crystalline molecular sieves have a 3-dimensional, four-connected framework structure of corner-sharing [TO$_4$] tetrahedra, where T is any tetrahedrally coordinated cation. In the case of silicoaluminophosphates (SAPOs), the framework structure is composed of [SiO$_4$], [AlO$_4$] and [PO$_4$] corner sharing tetrahedral units.

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types*, 5th edition, Elsevier, London, England (2001), which is herein fully incorporated by reference.

Non-limiting examples of the molecular sieves for which a structure has been established include the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework-type selected from the group consisting of AFO, AEL, EUO, HEU, FER, MEL, MFI, MTW, MTT, TON, and substituted forms thereof; and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD.

Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON.

Molecular sieve are typically described in terms of the size of the ring that defines a pore, where the size is based on the number of T atoms in the ring. Small pore molecular sieves generally have up to 8-ring structures and an average pore size less than 5 Å, whereas medium pore molecular sieves generally have 10-ring structures and an average pore size of about 5 Å to about 6 Å. Large pore molecular sieves generally have at least 12-ring structures and an average pore size greater than about 6 Å. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B. V., Amsterdam, Netherlands (2001).

Conveniently, the silicoaluminophosphate molecular sieve produced by the method of the invention is a small pore material including an AEI topology or a CHA topology, such as SAPO-18 or SAPO-34. Preferably, the molecular sieve includes at least one intergrowth of an AEI framework type material and a CHA framework type material.

Regular silicoaluminophosphate molecular sieves, such as SAPO-18 and SAPO-34, are built from structurally invariant building units, called Periodic Building Units, and are periodically ordered in three dimensions. Structurally disordered structures show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

The intergrown silicoaluminophosphate molecular sieves described herein are disordered planar intergrowth of end-member structures AEI and CHA. For AEI and CHA structure types, the Periodic Building Unit is a double six-ring layer. There are two types of layers "a" and "b", which are topologically identical except "b" is the mirror image of "a". When layers of the same type stack on top of one another, i.e. . . . aaa . . . or . . . bbb . . . , the framework type CHA is generated. When layers "a" and "b" alternate, e.g. . . . abab . . . , a different framework type, namely AEI, is generated. The intergrown molecular sieves described herein comprise stackings of layers "a" and "b" containing regions of CHA framework type and regions of AEI framework type. Each change of CHA to AEI framework type is a stacking disorder or planar fault.

In the case of crystals with planar faults, the interpretation of X-ray diffraction patterns requires an ability to simulate the effects of stacking disorder. DIFFaX is a computer program based on a mathematical model for calculating intensities from crystals containing planar faults (see M. M. J. Tracey et al., Proceedings of the Royal Chemical Society, London, A [1991], Vol. 433, pp. 499–520). DIFFaX is the simulation program selected by and available from the International Zeolite Association to simulate the XRD powder patterns for intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA and KFI, as reported by K. P. Lillerud et al. in "Studies in Surface Science and Catalysis", 1994, Vol. 84, pp.543–550.

Figure 1B:
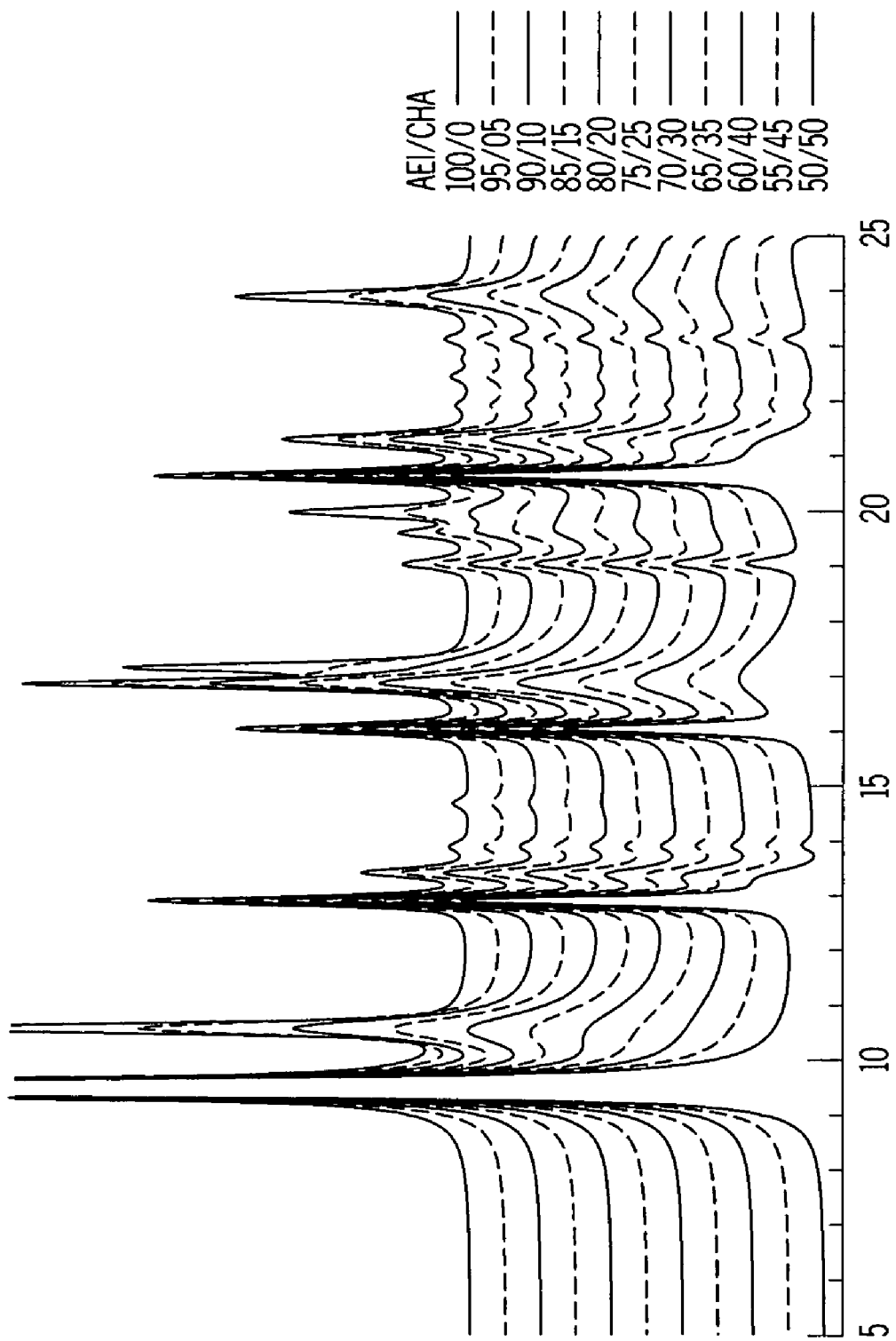

FIGS. 1*a* and 1*b* show the simulated diffraction patterns obtained for intergrowths of a CHA framework type molecular sieve with an AEI framework type molecular sieve having various AEI/CHA ratios. FIG. 1*a* shows the diffraction patterns in the 15 to 35 (2θ) range simulated by DIFFaX for intergrown phases with AEI/CHA ratios of 0/100 (CHA end-member), 10/90 (AEI/CHA=0.11), 20/80 (AEI/CHA=0.25), 30/70 (AEI/CHA=0.41), 40/60 (AEI/CHA=0.67), 50/50 (AEI/CHA=1.00) and 60/40 (AEI/CHA=1.50). FIG. 1*b* shows the diffraction patterns in the range of 5 to 20 (2θ) simulated by DIFFaX for intergrown phases with AEI/CHA ratios of 0/100 (CHA end-member), 10/90 (AEP/CHA=0.11), 20/80 (AEI/CHA=0.25), 50/50 (AEI/CHA=1.0), 70/30 (AEI/CHA=2.33), 80/20 (AEI/CHA=4.0),100/0 (AEI end-member). All XRD diffraction patterns are normalized to the highest peak of the entire set of simulated patterns, i.e. the peak at about 9.5 degrees 2θ for pure CHA (AEI/CHA ratio of 0/100). Such normalization of intensity values allows a quantitative determination of mixtures of intergrowths.

As the ratio of AEI increases relative to CHA in the intergrown phase, one can observe a decrease in intensity of certain peaks, for example, the peak at about 2θ=25.0 and an increase in intensity of other peaks, for example the peak at about 2θ=17.05 and the shoulder at 2θ=21.2. Intergrown phases with AEI/CHA ratios of 50/50 and above (AEI/CHA≧1.0) show a broad feature centered at about 16.9 (2θ).

In a preferred embodiment, the intergrown silicoaluminophosphate molecular sieve produced by the method of the invention is at least one intergrowth of an AEI framework type and a CHA framework type, wherein said at least one intergrowth has an AEI/CHA ratio of from about 5/95 to about 40/60, for example from about 10/90 to about 30/70, such as from about 15/85 to about 20/80, as determined by DIFFaX analysis. Such a CHA-rich intergrowth is characterized by a powder XRD diffraction pattern (obtained from a sample after calcination and without rehydration after calcination) having at least the reflections in the 5 to 25 (2θ) range as shown in Table below.

TABLE 1

| 2θ (CuKα) |
|---|
| 9.3–9.6 |
| 12.7–13.0 |
| 13.8–14.0 |
| 15.9–16.1 |
| 17.7–18.1 |
| 18.9–19.1 |
| 20.5–20.7 |
| 23.7–24.0 |

The X-ray diffraction data referred to herein are collected with a SCINTAG X2 X-Ray Powder Diffractometer (Scintag Inc., USA), using copper K-alpha radiation. The diffraction data are recorded by step-scanning at 0.02 degrees of two-theta, where theta is the Bragg angle, and a counting time of 1 second for each step. Prior to recording of each experimental X-ray diffraction pattern, the sample must be in the anhydrous state and free of any-template used in its synthesis, since the simulated patterns are calculated using only framework atoms, not extra-framework material such as water or template in the cavities. Given the sensitivity of silicoaluminophosphate materials to water at recording temperatures, the molecular sieve samples are calcined after preparation and kept moisture-free according to the following procedure.

About 2 grams of each molecular sieve sample are heated in an oven from room temperature under a flow of nitrogen at a rate of 3° C./minute to 200° C. and, while retaining the nitrogen flow, the sample is held at 200° C. for 30 minutes and the temperature of the oven is then raised at a rate of 2° C./minute to 650° C. The sample is then retained at 650° C. for 8 hours, the first 5 hours being under nitrogen and the final 3 hours being under air. The oven is then cooled to 200° C. at 30° C./minute and, when the XRD pattern is to be recorded, the sample is transferred from the oven directly to a sample holder and covered with Mylar foil to prevent rehydration. Recording under the same conditions immediately after removal of the Mylar foil will also provide a diffraction pattern suitable for use in DIFFaX analysis.

In an alternative embodiment, the intergrown silicoaluminophosphate molecular sieve produced by the method of the invention comprises a plurality of intergrown forms of the CHA and AEI framework types, typically with a first intergrown form having an AEI/CHA ratio of from about 5/95 to about 40/60, as determined by DIFFaX analysis, and a second intergrown form having a different AEI/CHA ratio from said first intergrown form. The second intergrown form typically has an AEI/CHA ratio of about 30/70 to about 55/45, such as about 50/50, as determined by DIFFaX analysis, in which case the XRD diffraction pattern exhibits a broad feature centered at about 16.9 (2θ) in addition to the reflection peaks listed in Table 1.

Preferably, the CHA framework type molecular sieve in the AEI/CHA intergrowths described above is SAPO-34 and the AEI framework type molecular sieve is selected from SAPO-18, ALPO-18 and mixtures thereof. In addition, the intergrown silicoaluminophosphate preferably has a framework silica to alumina molar ratio ($Si/Al_2$) greater than 0.16 and less than 0.19, such as from about 0.165 to about 0.185, for example about 0.18. The framework silica to alumina molar ratio is conveniently determined by NMR analysis.

Molecular Sieve Synthesis

Generally, silicoaluminophosphate molecular sieves are synthesized by the hydrothermal crystallization of a source of aluminum, a source of phosphorus, a source of silicon and at least one organic directing agent. Typically, a combination of sources of silicon, aluminum and phosphorus, together with one or more directing agents and optionally seeds from another or the same framework type molecular sieve, is placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

Non-limiting examples of suitable silicon sources include silicates, fumed silica, for example, Aerosil-200 available from Degussa Inc., New York, N.Y., and CAB-O-SIL M-5, organosilicon compounds such as tetraalkyl orthosilicates, for example, tetramethyl orthosilicate (TMOS) and tetraethylorthosilicate (TEOS), colloidal silicas or aqueous suspensions thereof, for example Ludox HS-40 sol available from E.I. du Pont de Nemours, Wilmington, Del., silicic acid or any combination thereof.

Non-limiting examples of suitable aluminum sources include organoaluminum compounds such as aluminum alkoxides, for example aluminum isopropoxide, and inorganic aluminum sources, such as aluminum phosphate, aluminum hydroxide, sodium aluminate, pseudo-boehmite, gibbsite and aluminum trichloride, or any combination thereof. Preferred sources are inorganic aluminum compounds, such as hydrated aluminum oxides and particularly boehlmite and pseudoboehmite.

Non-limiting examples of suitable phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A preferred source of phosphorus is phosphoric acid.

The organic directing agents employed in the synthesis of silicoaluminophosphate molecular sieves generally contain at least one element of Group 15 of the Periodic Table of Elements and at least one alkyl or aryl group, such as an alkyl or aryl group having from 1 to 10 carbon atoms, for example from 1 to 8 carbon atoms. Preferred directing agents are basic nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of suitable directing agents include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'- dimethylpiperazine, 1,4-diazabicyclo(2,2,2)octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2) octane ion; di-n-butylamine, neopentylamine, di-n-pentylamine, isopropylamine, t-butylamine, ethylenediamine, pyrrolidine, and 2-imidazolidone.

Since the organic directing agent used in the synthesis of silicoaluminophosphates is typically a basic nitrogen compound, whereas an attractive phosphorus source is phosphoric acid, it will be appreciated that the mixing of these materials can generate heat and hence raise the temperature of the synthesis mixture. According to the invention, it has been found that such a rise in temperature can lead to undesirable side reactions and possible production of impurity phases if the aluminum source is present, and more particularly if both the aluminum and silicon sources are present, in the synthesis mixture or are added thereto before the mixture has been allowed to cool.

To alleviate the above-mentioned problem, the synthesis mixture in the method of the invention is prepared by initially combining the source of phosphorus with at least one organic directing agent; and then cooling the combination of the phosphorus source and organic directing agent prior to introducing a source of aluminum into the combination. The cooling is arranged to lower the temperature of the synthesis mixture to less than or equal to 50° C., such as less than or equal to 40° C., for example about 10° C. to 40° C., preferably less than or equal to 30° C., for example about 10° C. to 30° C., before the aluminum source is added. The silicon source can be introduced into the combination of the phosphorus source and organic directing agent before, after or simultaneously with the aluminum source, but is normally added after cooling of the combination.

After combining all the components of the synthesis mixture, the mixture is desirably allowed to age at a temperature of between about 10° C. and about 30° C. for a time up to about 12 hours. Conveniently, the synthesis mixture is agitated during the aging step.

After the optional aging step, the synthesis mixture is sealed in a vessel and heated, preferably under autogenous pressure, to a temperature in the range of from 100° C. to about 350° C., for example from about 125° C. to about 250° C., such as from about 150° C. to about 200° C. The time required to form the crystalline product is usually dependent on the temperature and can vary from immediately up to several weeks. Typically the crystallization time is from about 30 minutes to around 2 weeks, such as from about 45 minutes to about 240 hours, for example from about 1 hour to about 120 hours. The hydrothermal crystallization may be carried out without or, more preferably, with agitation.

Once the crystalline molecular sieve product is formed, usually in a slurry state, it may be recovered by any standard technique well known in the art, for example, by centrifugation or filtration. The recovered crystalline product may then be washed, such as with water, and then dried, such as in air.

In one practical embodiment, wherein the silicoaluminophosphate molecular sieve comprises a CHA/AEI intergrowth as described above, the synthesis method comprises:

a) combining sources of silicon, phosphorus and aluminum with an organic structure directing agent (template) in the manner described above to form a mixture having a molar composition within the following ranges:

$P_2O_5$:$Al_2O_3$ from about 0.6 to about 1.2,
$SiO_2$:$Al_2O_3$ from about 0.005 to about 0.35,
$H_2O$:$Al_2O_3$ from about 10 to about 50;

b) mixing and heating the mixture (a) continuously to a crystallization temperature, such as between about 100° C. and about 250° C., typically between about 140° C. and about 180° C., preferably between about 150° C. and about 170° C.;

c) maintaining the mixture at the crystallization for a period of time of from 2 to 150 hours; such as from about 5 to about 100 hours, for example from about 10 to about 50 hours; and (d) recovering a crystalline product containing the desired molecular sieve.

As a result of the synthesis process, the crystalline product recovered such as in step (d) above contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system.

Molecular Sieve Catalyst Compositions

The silicoaluminophosphate molecular sieves produced by the synthesis method of the invention are particularly intended for use as organic conversion catalysts. Before use in catalysis, the molecular sieves will normally be formulated into catalyst compositions by combination with other materials, such as binders and/or matrix materials, which provide additional hardness or catalytic activity to the finished catalyst.

Materials which can be blended with the molecular sieve can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of molecular sieve contained in the final catalyst product ranges from 10 to 90 weight percent of the total catalyst, preferably 20 to 80 weight percent of the total catalyst composition.

Use of the Molecular Sieve

The silicoaluminophosphate molecular sieves produced by the method of the invention are useful as catalysts in a variety of processes including cracking of, for example, a naphtha feed to light olefin(s) or higher molecular weight (MW) hydrocarbons to lower MW hydrocarbons; hydrocracking of, for example, heavy petroleum and/or cyclic feedstock; isomerization of, for example, aromatics such as xylene; polymerization of, for example, one or more olefin(s) to produce a polymer product; reforming; hydrogenation; dehydrogenation; dewaxing of, for example, hydrocarbons to remove straight chain paraffins; absorption of, for example, alkyl aromatic compounds for separating out isomers thereof; alkylation of, for example, aromatic hydrocarbons such as benzene and alkyl benzene, optionally with propylene to produce cumene or with long chain olefins; transalkylation of, for example, a combination of aromatic and polyalkylaromatic hydrocarbons; dealkylation; dehydrocyclization; disproportionation of, for example, toluene to make benzene and paraxylene; oligomerization of, for example, straight and branched chain olefin(s); and dehydrocyclization.

Where the silicoaluminophosphate is an AEI or CHA structure type material or an intergrowth of an AEI structure type material and a CHA structure type material, the molecular sieve produced by the method of the invention is particularly suitable as a catalyst for use in the conversion of oxygenates to olefins. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising-the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as in the range of from about 0.5 $hr^{-1}$ to about 300 $hr^{-1}$, for example in the range of from about 0.1 $hr^{-1}$ to about 200 $hr^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

Using the various oxygenate feedstocks discussed above, particularly a feedstock containing methanol, a catalyst composition of the invention is effective to convert the feedstock primarily into one or more olefin(s). The olefin(s) produced typically have from 2 to 30 carbon atoms, preferably 2 to 8 carbon atoms, more preferably 2 to 6 carbon atoms, still more preferably 2 to 4 carbons atoms, and most preferably are ethylene and/or propylene. The resultant olefins can be separated from the oxygenate conversion product for sale or can be fed to a downstream process for converting the olefins to, for example, polymers.

The invention will now be more particularly described with reference to the following Examples.

In the Examples, DIFFaX analysis was used to determine the AEI/CHA ratio of the molecular sieves. Simulated powder XRD diffraction patterns for varying ratios of AEI/CHA were generated using the DIFFaX program available from the international Zeolite Association (see also M. M. J. Tracey et al., Proceedings of the Royal Chemical Society, London, A (1991), Vol. 433, pp. 499–520 "Collection of Simulated XRD Powder Patterns for Zeolites" by M. M. J. Treacy and J. B. Higgins, 2001, Fourth Edition, published on behalf of the Structure Commission of the International Zeolite Association). The DIFFaX input file used to simulate the XRD diffraction patterns is given in Table 2 of U.S. Patent Application Publication No. 2002/0165089, incorporated herein by reference. In order to obtain best fitting between the DIFFaX simulated patterns and the experimental patterns, two sets of simulated XRD patterns were generated using a line broadening of 0.009 (as described in U.S. Patent Application No. 2002/0165089) and a line broadening of 0.04 (FIGS. 1a and 1b). The simulated diffraction patterns were then compared with the experimental powder XRD diffraction patterns. In this respect, a very sensitive range is the 15 to 19.5 2θ range.

EXAMPLE 1

A mixture of 5017 kg of phosphoric acid (85% in water), 4064 kg of demineralized water and 9157 kg of tetraethylammonium hydroxide solution (35% in water, Sachem) was prepared. After initiating stirring of the mixture and cooling the mixture to 30° C., 392 kg Ludox AS 40 (40% silica) was added to the beaker followed by 2873 kg of alumina (Condea Pural SB-1) and 422 kg of rinse water. The composition of the final synthesis mixture in terms of molar ratios was as follows:

0.12SiO$_2$/Al$_2$O$_3$/P$_2$O$_5$/TEAOH/34H$_2$O

The mixture was transferred to a stainless steel autoclave and heated at a rate of 20° C./hour to 165° C. while being stirred with a mixer at a speed of 31 rpm. The autoclave was kept at 165° C. for 72 hours. After cooling to room temperature, the slurry was washed. The washed slurry had a d$_{50}$ particle size of 1.7 μm, as measured with a Malvern Mastersizer 2000 (d$_{50}$ expressed by volume). The washed slurry was then dried and an X-ray diffraction pattern of the crystalline product was taken after the calcination procedure described above. Using this diffraction pattern, DIFFaX analysis was conducted and showed the crystalline product to contain an AEI/CHA intergrowth comprising 26 wt % of an AEI structure type molecular sieve and 74 wt % of a CHA structure type molecular sieve. The silica to alumina molar ratio (Si/Al$_2$) of the crystalline product was found to be 0.16 and the yield of the AEI/CHA intergrowth was 20.2 wt % of the solids in the starting mixture.

EXAMPLES 2 to 6

The procedure of Example 1 was repeated but with the mixture of phosphoric acid, demineralized water and tetraethylammonium hydroxide solution being cooled to various temperatures between 10° C. and 50° C. before addition of the silica and alumina. Apart from some minor changes in the rate of beating to the crystallization temperature of 165° C., all the other parameters of Example 1 remained the same. The results are summarized in Table 2, where "Other" designates any impurity phases present in the crystalline product as determined by the X-ray analysis and "Cooling Temp" indicates the temperature to which the mixture of phosphoric acid, demineralized water and tetraethylammonium hydroxide solution was cooled before addition of the silica and alumina.

TABLE 2

| Ex | Cooling Temp. ° C. | Heat Rate ° C./hr | Yield wt % | AEI/CHA | Other | Al$_2$/Si Product |
|---|---|---|---|---|---|---|
| 2 | 10 | 23 | 20.0 | 25/75 | AFI | 0.16 |
| 3 | 15 | 20 | 20.4 | 24/76 |  | 0.15 |
| 4 | 20 | 21 | 19.7 | 27/73 |  | 0.15 |
| 5 | 40 | 20 | 20.1 | 26/74 | APC | 0.16 |
| 6 | 50 | 20 | 22.5 | 30/70 |  | 0.14 |

EXAMPLES 7 and 8

The procedure of Example 1 was repeated but with the crystallization time at 165° C. being either 48 hours (Example 7) or 60 hours (Example 8), all the other parameters of Example 1 remaining the same. As in Example 1, the mixture of phosphoric acid, demineralized water and tetraethylammonium hydroxide solution was cooled to 30° C. before addition of the silica and alumina. The results are summarized in Table 3, where "Other" designates any impurity phases present in the crystalline product as determined by X-ray, analysis.

TABLE 3

| Ex | Heat Rate ° C./hr | Yield wt % | AEI/CHA | Other | Al$_2$/Si Product |
|---|---|---|---|---|---|
| 7 | 20 | 19.5 | 30/70 | APC | 0.15 |
| 8 | 20 | 20.2 | 27/73 |  | 0.16 |

EXAMPLE 9 (COMPARATIVE)

8221.1 g of phosphoric acid (85% in water) was diluted with 6693.8 g of demineralized water. To this solution was added 535.6 g of Ludox. AS40 (40% silica in water) and 147.1 g of water. After mixing until homogeneous, 15001.3 g of tetraethylammonium hydroxide solution (35% in water, Sachem) and 147.1 g of demineralized water were added and the mixture was stirred until homogeneous. Then 4886.2 g of alumina (Condea Pural SB-1) and 367.8 g of rinse water were added. The temperature of the mixture was 53 C. The composition of the final synthesis mixture in terms of molar ratios was as follows:

0.10SiO$_2$/Al$_2$O$_3$/P$_2$O$_5$/TEAOH/34H$_2$O

The mixture was transferred to a stainless steel autoclave and heated in 12 hrs to to 175° C. while being stirred with a mixer at a speed of 49 rpm. The autoclave was kept at 175° C. for 17 hours. After cooling to room temperature, the slurry was washed. The washed slurry was then dried and an X-ray diffraction pattern of the crystalline product was taken. The product was identified to be a mixture of SAPO-5 and SAPO-34.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A method of synthesizing a silicoaluminophosphate molecular sieve, the method comprising:
   (a) preparing a synthesis mixture comprising the steps of:
      (i) combining a source of phosphorus and at least one organic directing agent, wherein the mixing of said phosphorus source and said organic directing agent can generate heat and raise the temperature of said synthesis mixture; and
      (ii) cooling the combination of the phosphorus source and organic directing agent to a temperature of less than or equal to 50° C., prior to introducing a source of aluminum into the combination;
   (b) heating said synthesis mixture comprising said source of phosphorus, said at least one organic directing agent, said source of aluminum and a source of silicon to a crystallization temperature of between about 100° C. and about 300° C.; and
   (c) recovering said molecular sieve.

2. The method of claim 1, wherein said combination of the phosphorus source and organic directing agent is cooled to a temperature of less than 40° C., prior to introducing a source of aluminum into the combination.

3. The method of claim 1, wherein said combination of the phosphorus source and organic directing agent is cooled to a temperature between about 10° C. and about 40° C., prior to introducing a source of aluminum into the combination.

4. The method of claim 1, wherein said combination of the phosphorus source and organic directing agent is cooled to a temperature of less than 30° C., prior to introducing a source of aluminum into the combination.

5. The method of claim 1, wherein said combination of the phosphorus source and organic directing agent is cooled to a temperature between about 10° C. and about 30° C., prior to introducing a source of aluminum into the combination.

6. The method of claim 1, wherein said source of aluminum is an inorganic aluminum compound.

7. The method of claim 1, wherein said source of aluminum is a hydrated aluminum oxide.

8. The method of claim 1, wherein said source of aluminum is boehmite or pseudoboehmite.

9. The method of claim 1, wherein preparing said synthesis mixture further comprises introducing said source of silicon into said combination of the phosphorus source and organic directing agent after said cooling.

10. The method of claim 9, wherein the source of silicon is introduced into said combination of the phosphorus source and organic directing agent prior to introduction of said source of aluminum.

11. The method of claim 9, wherein the source of silicon is introduced into said combination of the phosphorus source and organic directing agent after introduction of said source of aluminum.

12. The method of claim 1, wherein said source of phosphorus is phosphoric acid.

13. The method of claim 1, wherein said organic directing agent is a nitrogen compound.

14. The method of claim 1 and further comprising allowing said synthesis mixture to age at a temperature of between about 10° C. and about 30° C. for a time up to about 12 hours.

15. The method of claim 14 and further comprising agitating said synthesis mixture during aging thereof.

16. The method of claim 1 and further comprising agitating said synthesis mixture during (a) and/or (b).

17. The method of claim 1, wherein said silicoaluminophosphate molecular sieve comprises at least one of an AEI structure type molecular sieve and a CHA structure type molecular sieve.

18. The method of claim 1, wherein said silicoaluminophosphate molecular sieve comprises at least one intergrown phase of an AEI structure type molecular sieve and a CHA structure type molecular sieve.

19. The method of claim 18, wherein said at least one intergrown phase has an AEI/CHA ratio of from about 5/95 to about 40/60 as determined by DIFFaX analysis.

20. The method of claim 18, wherein said at least one intergrown from has an AEI/CHA ratio of from about 10/90 to about 30/70 as determined by DIFFaX.

21. The method of claim 18, wherein said at least one intergrown form has an AEI/CHA ratio of from about 15/95 to about 20/80 as determined by DIFFaX.

22. The method of claim 18, wherein said silicoaluminophosphate molecular sieve has an X-ray diffraction pattern comprising at least one reflection peak in each of the following ranges in the 5 to 25 (2θ) range:

| 2θ (CuKα) |
| --- |
| 9.3–9.6 |
| 12.7–13.0 |
| 13.8–14.0 |
| 15.9–16.1 |
| 17.7–18.1 |
| 18.9–19.1 |
| 20.5–20.7 |
| 23.7–24.0. |

23. The method of claim 1, wherein said silicoaluminophosphate molecular sieve comprises first and second intergrown forms each of an AEI framework type material and a CHA framework type material.

24. The method of claim 23, wherein said first intergrown form has an AEI/CHA ratio of from about 5/95 to about 40/60 as determined by DIFFaX analysis and said second intergrown form has a different AEI/CHA ratio from said first intergrown form.

25. The method of claim 24, wherein said second intergrown form has an AEI/CHA ratio of about 30/70 to about 55/45 as determined by DIFFaX analysis.

26. The method of claim 24, wherein said second intergrown form has an AEI/CHA ratio of about 50/50 as determined by DIFFaX analysis.

* * * * *